United States Patent [19]

Noller

[11] Patent Number: 4,668,868
[45] Date of Patent: May 26, 1987

[54] APPARATUS FOR PERFORMING FLUOROIMMUNOASSAYS OF BIOLOGICAL SPECIMENS

[76] Inventor: Hans T. Noller, 424 E. Church La., Philadelphia, Pa. 19144

[21] Appl. No.: 831,324

[22] Filed: Feb. 20, 1986

[51] Int. Cl.$^4$ ............................................. G01N 21/64
[52] U.S. Cl. .............................. 250/458.1; 250/461.2; 356/417
[58] Field of Search ............... 250/461.1, 461.2, 458.1, 250/365; 356/317, 318, 417

[56] References Cited

U.S. PATENT DOCUMENTS 4,100,416  7/1978  Hirschfeld ..................... 250/461.2

Primary Examiner—Carolyn E. Fields
Attorney, Agent, or Firm—Edward A. Sokolski

[57] ABSTRACT

The output of a light source preferably of a fluorescent lamp is filtered to provide light energy in a predetermined spectrum and this light energy used to excite a biological specimen which may comprise antigens and antibodies which are tagged with flurorescent material. Light energy at a predetermined frequency is emitted by the fluorescent material in response to this excitation, the magnitude of this light energy representing the population of the biological specimen of interest. This light energy is used to excite a photovoltaic cell which produces an electrical output in accordance with the excitation thereof. Compensation for temperature drift and other offset voltages which might be developed in the photovoltaic cell is provided by means of a second mating photovoltaic cell from which light excitation is eliminated, the output of this second photovoltaic cell being used as a compensating bias voltage to eliminate voltage outputs due to temperature drift and other offset voltages. The output of the first photovoltaic cell is amplified and fed to an appropriate volt-meter for a readout indication. Compensation is also provided in the amplifier for drift correction by means of a push button calibrator which is used to provide a compensating bias voltage in accordance with the output of the photovoltaic cell with zero input signal which is memorized and then subtracted from the peak signal voltage detected from the fluorotagged specimen.

7 Claims, 3 Drawing Figures

APPARATUS FOR PERFORMING FLUOROIMMUNOASSAYS OF BIOLOGICAL SPECIMENS

This invention relates to an apparatus for performing fluoroimmunoassays and more particularly, such a device suitable for performing such assays of biological specimens which employs photovoltaic detectors with compensating circuitry for minimizing the effects of temperature drift and other offset error voltages.

The use of fluorescent tags in performing immunoassays for use for example in determining the antibody population in a specimen is well known in the art and is described for example in U.S. Pat. Nos. 4,187,075, 4,133,873 and 4,451,149 to Hans G. Noller. In the apparatus described in the prior art, photomultiplier detectors are employed to detect the light energy output from the specimen which is in accordance with the fluorescently tagged population of such specimen. Such photomultiplier detectors have been found necessary in prior art devices to provide sufficient voltage output to afford useable readings. Such photomultiplier devices are relatively costly and require fairly expensive power supplies. The apparatus of the present invention is an improvement over prior art devices such as described in the aforementioned patents in that it enables the use of relatively inexpensive photovoltaic cells for detecting the light energy and obviates the need for expensive photomultiplier devices and their associated power supplies without sacrificing accuracy.

Photovoltaic cells have not been employed in prior art fluoroimmunoassay equipment principally because of their relatively low sensitivity and their susceptibility to temperature drift and other offset voltages which has made their accuracy questionable.

The apparatus of the present invention overcomes the aforementioned shortcomings attributable to photovoltaic cells and enables their employment in fluoroimmunoassay apparatus by means of several novel improvements provided in the apparatus of the present invention. First to compensate for the lower sensitivity, of the photovoltaic cell employed, to avoid losses in light energy which are a function of the square of the distance such light energy travels the detection apparatus has been designed so that all elements of the system are in close proximity to each other. Thus, the light source and associated filters, the specimen to be assayed, and the filter and detector for detecting the fluorescent output of the specimen are all placed in close proximity to each other so that light losses are minimized. Secondly, a unique compensation circuit is provided to minimize the effects of temperature drift in the output of the detector as well as other offset errors. This is afforded by providing a reference detector which is a mating twin of the signal detector but which has all light input thereto blocked out by blackening the detection surface or other suitable means. The output of this reference detector is then fed as a compensating bias voltage to one of the polarity inputs of an operational amplifier with the output of the signal detector being fed to the other polarity input of this amplifier thereby tending to bias out any temperature drift for other offset voltages present in the signal detector output. In addition, a push button calibration circuit is employed whereby the "no signal" output of the just mentioned operational amplifier is memorized and then subtracted from the full signal output of this amplifier in a compensating circuit. In this manner, substantially all of the temperature drift and other offset voltages present in the detector output are eliminated so that the output of the fluorescent tagged molecules is accurately reflected in the readout. Incorporation of a unique signal-peak-holding subsystem, which can be zeroed by the same push button action, allows it to store and to display the reading of every sample until the instrument is ready for the next sample.

It is therefore an object of this invention to enable the use of relatively inexpensive components without sacrificing accuracy in fluoroimmunoassay apparatus.

It is still a further object of this invention to enable utilization of photovoltaic cells in detecting fluoro-tagged biological without sacrificing the accuracy of the output signals obtained.

Other objects of this invention will become apparent as the description proceeds in connection with the accompanying drawings of which:

Figure 1:
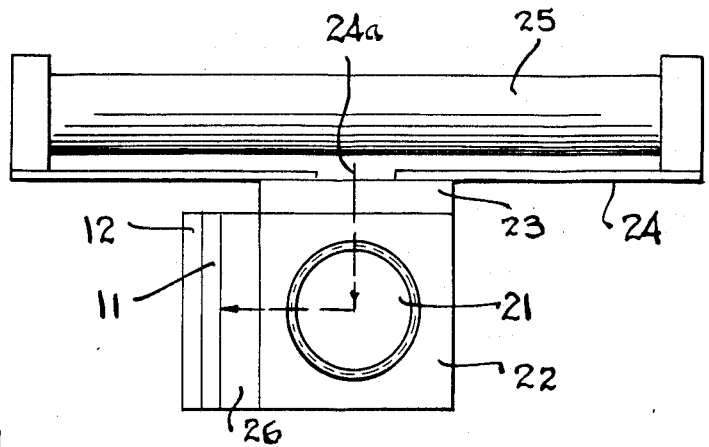
FIG. 1 is a top plan view of a preferred embodiment of the invention.
Figure 2:
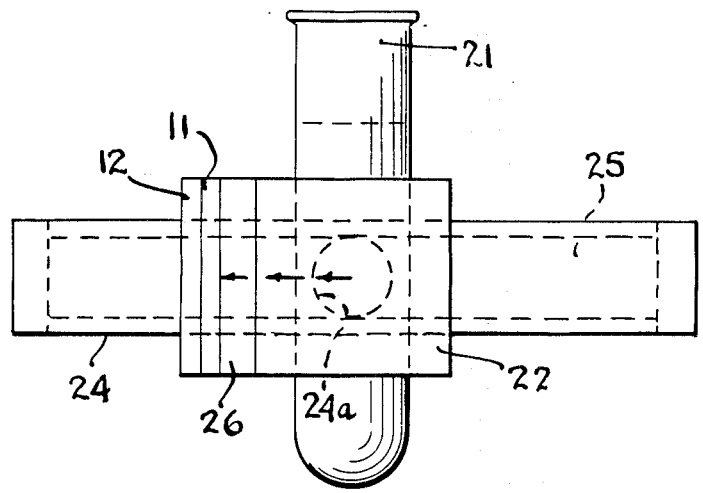
FIG. 2 is a side elevational view of the preferred embodiment.

Referring now to FIGS. 1 and 2 a preferred embodiment of the invention is illustrated. Fluorescent lamp 25 which may be a black light source having emission in the ultraviolet range is mounted in an optically opaque frame member 24 having a slit 24a formed therein. Immediately adjacent to the light source and the frame is the excitation light filter 23 which passes light energy for instance in the 300–400 millimicron band. Immediately adjacent to light filter 23 is a transparent holder 22 in which transparent tube 21 is retained, this tube containing the specimen or sample to be assayed. The molecules of the biological species in the specimen are tagged with fluorophors, these fluorophors emitting light in the emission light band when excited by the light energy which passes filter 23. Immediately adjacent to tube holder 22 and oriented 90 degress off from the light filter 23 is an interference filter 26 which passes the light energy which is emitted from the sample for instance in the 450 millimicron range (i.e. in the blue spectrum). Immediately adjacent to light filter 26 is photovoltaic cell 11 which has its sensitive surface facing the light energy and which generates an output voltage in accordance with the light energy received thereby. Mounted immediately adjacent to photovoltaic cell 11 is a similar mating voltaic cell 12 which has its light sensitive surface made light opaque as for example by blackening so that it does not receive any light input. Fluorescent lamp 25 may be a Sylvania type F4TS/BL 4 watt black light while photovoltaic cells 11 and 12 may be type S2L selenium photovoltaic cells available from Vactec, Inc., St. Louis, Mo.

Figure 3:
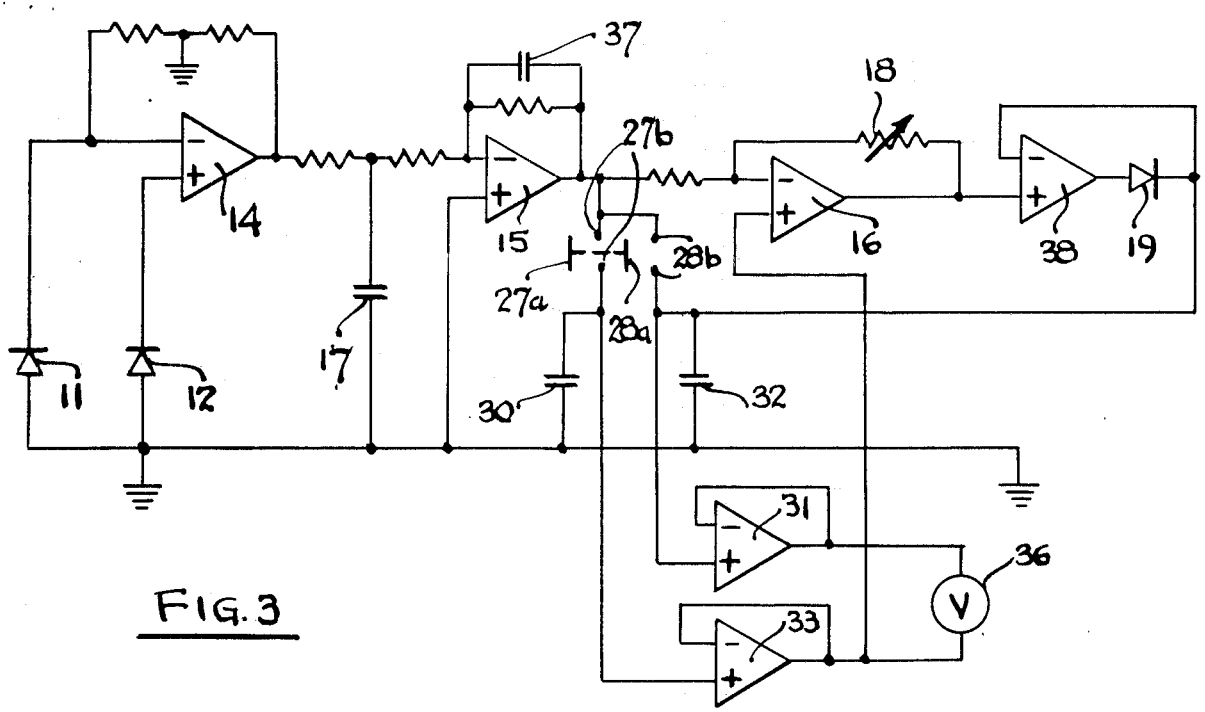
FIG. 3 is a schematic drawing illustrating the circuitry employed in the preferred embodiment.

Referring now to FIG. 3, the circuitry employed to provide an output reading in response to the signals received by photovoltaic cell 11 is schematically illustrated. The anodes of photovoltaic cells 11 and 12 are grounded, the cathode of cell 11 being connected to the inverting input of operational amplifier 14 while the cathode of photovoltaic cell 12 is connected to the non-inverting input of this operational amplifier. Thus, the output of photovoltaic cell 12 which represents any offset voltage present including outputs due to temperature variations is fed to the amplifier so as to cancel out any similar offset voltages present in the output of photovoltaic cell 11. Amplifier 14 is an ultra high gain amplifier and substantially amplifies the output of photovoltaic cell 11. The output of the operational amplifier 14 appears across capacitor 17. The output of operational amplifier 14 which represents the signal voltage to be measured is fed to the inverting input of operational amplifier 15 which operates to condition the signal by eliminating through the filtering action of capacitors 17 and 37 stray AC which may have been picked up in the high impedance input circuit of operational amplifier 14. The output of conditioning amplifier 15 is fed to the inverting input of operational amplifier 16 the gain of which is controllable by means of variable resistor 18, this variable resistor being useful for calilbration purposes. The output of amplifier 16 is fed into the peak-point holding subsystem consisting of unity gain operational amplifier 38, diode 19, integrating capacitor 32 and unity gain operational amplifier 31, whose charge capacitor 32 can be brought to bias level before the measurement with activation of push button switch 27a and 28a. The peak of the sample dependant voltage which appears at the output of operational amplifier 16 is then derived by diode 19 operating in conjunction with unity gain operational amplifier 38 and is used to charge capacitor 32 which provides memory of such output. The voltage, across capacitor 32 is fed to the non-inverting input of operational amplifier 31. Operational amplifier 31 is a unity gain amplifier and provides a signal in accordance with the voltage to which capacitor 32 is charged to one of the terminals of voltmeter 36.

The voltage across integrating capacitor 30 is fed to the non-inverting input of operationl amplifier 33, this operational amplifier being a unity gain amplifier. The output of amplifier 33 is fed to the other terminal of voltmeter 36 and is fed also to the non-inverting input of operational amplifier 16, so supplying that operational amplifier with the temperature and supply voltage drift corrected bias voltage.

The circuitry including diode 19, capacitors 30 and 32, and operational amplifiers 31, 38 and 33 are used in conjunction with push button switches 27a and 28a to calibrate the circuit and to compensate for temperature drifts and other extraneous offset voltages which might appear in the output of photovoltaic cell 11. This circuitry operates as follows:

Without a sample in the sample tube holder 22, push button switches 27a and 28a are momentarily depressed to close contacts 27b and 28b respectively. This causes capacitor 30 to charge to the voltage at the output of operational amplifier 15 which represents a non signal "reference" value. Capacitor 30 is large enough and has low enough leakage to retain this charge for at least several minutes (e.g. 10 mfd). The test tube 21 containing the sample to be assayed is then placed in the tube holder 22. This will produce an output signal from operational amplifier 16 which is in accordance with the population of the tagged species in the sample. This output signal is fed through high reverse resistance diode 19, which may be formed by the base-collector junction of a transistor, to capacitor 32, and in a relatively short period (typically about 10 seconds) capacitor 32 is charged to the peak voltage of the operational amplifier output. This peak voltage is then fed through unity gain amplifier 31 to one of the terminals of voltmeter 36 while the voltage across capacitor 30, which represents the offset drift voltage of the photovoltaic cell, is fed through unity gain amplifier 33 to the other terminal of voltmeter 36. Thus, the voltmeter reads the differential between the peak voltage output and the offset temperature drift voltage, the unwanted offset drift voltage thus effectively being cancelled out of the output reading provided on voltmeter 36. The output of operational amplifier 33 is also fed to the non-inverting input of amplifier 16 to furnish that amplifier with the drift-corrected bias (or baseline-voltage).

It is to be noted that voltmeter 36 will continue to read the last measured sample even if the sample is removed from the holder, the circuit being reset for a further reading only when the pushbuttons 27a and 28a are depressed which provides a discharge path for capacitor 32 through contacts 28b.

While the invention has been described and illustrated in detail, it is to be clearly understood that this is intended by way of illustration and example only and is not to be taken by way of limitation, the spirit and scope of the invention being limited only by the terms of the following claims.

I claim:

1. Apparatus for determining the population of the fluorotagged molecules in a sample comprising
   light source means for generating light energy in the region of the excitation of said fluorotagged molecules,
   means for retaining said sample in close proximity to said light source means such that said light energy impinges thereon causing said fluorotagged molecules to radiate light energy at their emission wavelength,
   filter means immediately adjacent to said sample for passing light substantially only at the frequency of the light energy radiated by the fluorotagged molecules,
   first photovoltaic cell means immediately adjacent to said filter means for receiving the light energy passed therethrough from said sample,
   second photovoltaic cell means similar to said first photovoltaic cell means and positioned adjacent to said first photovoltaic cell means for providing a reference voltage representing temperature drift and offset voltage in the output of second cell means, said second photovoltaic cell means having a light sensing area which is blocked off to prevent the second cell means from sensing light energy,
   amplifier means for receiving the outputs of said first and second photovoltaic cell means and producing an electrical output in accordance with the difference therebetween,
   readout means for providing a readout in accordance with the output of said amplifier means, and
   calibration means including first means for memorizing a signal in accordance with the output of said amplifier means when no sample is being measured, second memorizing means for memorizing the output of said amplifier means when a sample is being measured, said readout means being connected to receive the outputs of said first and second memorizing means to read the differential therebetween.

2. The apparatus of claim 1 wherein said amplifier means comprises an operational amplifier having inverting and non-inverting inputs, the output of said first cell means being fed to one of said inputs, the output of said second cell means being fed to the other of said inputs.

3. The apparatus of claim 1 wherein said readout means comprises a voltmeter.

4. The apparatus of claim 1 wherein said calibration means comprises a momentary contact pushbutton switch having a first pair of contact means connected to momentarily feed the output of said amplifier means to said first memorizing means when said switch is activated.

5. The apparatus of claim 4 wherein said first and second memorizing means are integrating capacitors.

6. The apparatus of claim 4 wherein the pushbutton switch further has a second pair of contact means for removing the memorized output of said amplifier means from said second memorizing means when said switch is activated.

7. Apparatus for determining the population of the fluorotagged molecules in a sample comprising light source means for generating light energy in a region of sensitivity of said fluorotagged molecules, means for retaining said sample in close proximity to said light source means such that said light energy impinges thereon causing said fluorotagged molecules to radiate light energy at the emission wavelength of that fluorescent tag, filter means immediately adjacent to said sample for passing light substantially only at the frequency of the light energy radiated by the fluorotagged molecules, first photovoltaic cell means immediately adjacent to said filter means for receiving the light energy passed therethrough from said sample, second photovoltaic cell means similar to said first photovoltaic cell means and positioned adjacent to said first photovoltaic cell means for providing a reference voltage representing temperature drift and offset voltage in the output of said second cell means, said second photovoltaic cell means having a light sensing area which is blocked off to prevent the second cell means from sensing light energy, amplifier means for receiving the outputs of said first and second photovoltaic cell means and producing an electrical output in accordance with the difference therebetween, readout means for providing a readout in accordance with the output of said amplifier means, a first integrating capacitor, switch contact means for selectively connecting the output of said amplifier means to said first capacitor when there is no sample being measured to charge said capacitor to the peak voltage output of the amplifier means, a second integrating capacitor connected to charge to and store a voltage in accordance with the peak voltage output of said amplifier means when the switch contact means is not connecting the output of said amplifier means to said first capacitor, readout means, and means for coupling the outputs of said first and second integrating capacitors to said readout means in opposite polarity relationship such that the readout means generates a readout in accordance with the differential therebetween.

* * * * *